(12) United States Patent
Depenbusch

(10) Patent No.: US 11,395,762 B2
(45) Date of Patent: Jul. 26, 2022

(54) CATARACT PHACOEMULSIFICATION TIP

(71) Applicant: Michael Jerome Designs, LLC, Chandler, AZ (US)

(72) Inventor: Michael Jerome Depenbusch, Phoenix, AZ (US)

(73) Assignee: Michael Jerome Designs, LLC, Chandler, AZ (US)

( * ) Notice: Subject to any disclaimer, the term of this patent is extended or adjusted under 35 U.S.C. 154(b) by 556 days.

(21) Appl. No.: 16/403,091

(22) Filed: May 3, 2019

(65) Prior Publication Data

US 2019/0254871 A1    Aug. 22, 2019

Related U.S. Application Data

(63) Continuation of application No. 15/196,844, filed on Jun. 29, 2016, now abandoned.

(60) Provisional application No. 62/190,224, filed on Jul. 8, 2015.

(51) Int. Cl.
*A61F 9/007* (2006.01)
*A61M 1/00* (2006.01)

(52) U.S. Cl.
CPC .......... *A61F 9/00745* (2013.01); *A61M 1/85* (2021.05)

(58) Field of Classification Search
CPC ............................ A61F 9/00745; A61M 1/85
See application file for complete search history.

(56) References Cited

U.S. PATENT DOCUMENTS

| 3,589,363 | A | 6/1971 | Banko et al. |
| 4,623,327 | A | 11/1986 | Mahurkar |
| 4,747,820 | A | 5/1988 | Hornlein et al. |
| 4,924,882 | A | 5/1990 | Donovan |
| 5,403,307 | A | 4/1995 | Zelman |
| 5,476,450 | A | 12/1995 | Ruggio |

(Continued)

FOREIGN PATENT DOCUMENTS

| CN | 101119765 A | * | 2/2008 | ............ A61M 39/12 |
| EP | 0645161 A2 | * | 3/1995 | |

(Continued)

OTHER PUBLICATIONS

United States Office Action, U.S. Appl. No. 16/195,690, dated Jul. 13, 2020, eight pages.

(Continued)

*Primary Examiner* — Amy R Weisberg
(74) *Attorney, Agent, or Firm* — Fenwick & West LLP

(57) ABSTRACT

A phacoemulsification or aspiration tip is designed for use in cataract surgeries. The phacoemulsification tip (also referred to as a phaco tip) can reduce the duration and energy of cataract surgeries because the phaco tip is designed to reduce the likelihood that cataract fragments will become clogged inside the phaco tip. For example, the phaco tip has a lumen with variable sized diameters, which helps filter out larger cataract fragments that are more likely to clog the phaco tip. Further, the phaco tip can have a larger diameter at a bend to prevent blockages. The opening of the phaco tip can have a sharp edge to shear cataract fragments into smaller pieces that are less likely to clog the phaco tip. By preventing blockages using the phaco tip and reducing the duration of cataract surgeries, patients may recover faster from the cataract surgeries.

11 Claims, 7 Drawing Sheets

(56) References Cited

U.S. PATENT DOCUMENTS

| | | | |
|---|---|---|---|
| 5,478,338 A | 12/1995 | Reynard | |
| 5,718,676 A | 2/1998 | Barrett | |
| 5,725,495 A * | 3/1998 | Strukel | A61M 1/743 604/44 |
| 5,830,192 A | 11/1998 | Van Voorhis | |
| 5,836,959 A | 11/1998 | Seibel et al. | |
| 6,007,555 A | 12/1999 | Devine | |
| 6,280,423 B1 | 8/2001 | Davey et al. | |
| 6,551,557 B1 | 4/2003 | Rose et al. | |
| 7,588,553 B2 | 9/2009 | Dewey | |
| 9,492,634 B2 | 11/2016 | Moehle et al. | |
| 10,166,144 B2 | 1/2019 | Depenbusch | |
| 2001/0031951 A1 | 10/2001 | Pezzola | |
| 2004/0030303 A1 | 2/2004 | Prais et al. | |
| 2006/0253056 A1 * | 11/2006 | Kadziauskas | A61F 9/00745 602/22 |
| 2007/0231215 A1 | 10/2007 | Mototsu et al. | |
| 2008/0058708 A1 | 3/2008 | Akahoshi | |
| 2009/0041924 A1 | 2/2009 | Steube | |
| 2009/0099536 A1 | 4/2009 | Akahoshi | |
| 2009/0192440 A1 | 7/2009 | Akahoshi | |
| 2010/0010419 A1 | 1/2010 | Akahoshi | |
| 2010/0036388 A1 * | 2/2010 | Gomez | A61M 1/85 606/107 |
| 2010/0316542 A1 | 12/2010 | Mototsu et al. | |
| 2011/0066000 A1 | 3/2011 | Ibrahim et al. | |
| 2011/0112466 A1 | 5/2011 | Dimalanta | |
| 2012/0157934 A1 | 6/2012 | Liao et al. | |
| 2012/0191034 A1 | 7/2012 | Akahoshi | |
| 2013/0023918 A1 | 1/2013 | Morlet | |
| 2013/0096569 A1 | 4/2013 | Akahoshi | |
| 2014/0330286 A1 | 11/2014 | Wallace | |
| 2015/0196426 A1 | 7/2015 | Kuebler et al. | |
| 2015/0201958 A1 | 7/2015 | Krieger et al. | |
| 2015/0359547 A1 | 12/2015 | Vale et al. | |
| 2017/0001190 A1 | 1/2017 | Ito | |

FOREIGN PATENT DOCUMENTS

| | | | |
|---|---|---|---|
| EP | 1129681 A1 * | 9/2001 | A61F 9/00745 |
| EP | 1632204 A1 * | 3/2006 | A61F 9/00745 |
| WO | WO 2014/192584 A1 | 12/2014 | |

OTHER PUBLICATIONS

PCT International Search Report and Written Opinion, PCT Application No. PCT/US16/40048, dated Oct. 31, 2016, 15 pages.

PCT Invitation to Pay Additional Fees, PCT Application No. PCT/US16/40048, Sep. 1, 2016, 2 pages.

European Patent Office, Extended European Search Report and Opinion, EP Patent Application No. 16821825.3, dated Feb. 18, 2019, seven pages.

United States Office Action, U.S. Appl. No. 15/196,844, dated Dec. 20, 2018, 16 pages.

United States Office Action, U.S. Appl. No. 15/196,844, dated Aug. 6, 2018, nine pages.

\* cited by examiner

CATARACT PHACOEMULSIFICATION TIP

CROSS-REFERENCE TO RELATED APPLICATIONS

This application is a continuation of co-pending U.S. application Ser. No. 15/196,844, filed Jun. 29, 2016, which claims priority to U.S. Provisional Application No. 62/190,224 filed Jul. 8, 2015, each of which are incorporated by reference herein in their entirety.

BACKGROUND

1. Field of Art

This invention relates generally to the field of cataract surgery, and particularly to a phacoemulsification or aspiration tip used in cataract surgery.

2. Description of the Related Art

Cataract surgery involves removing the lens of a patient's eye that has become cloudy due to cataract formation, and replacing the lens with a clear artificial lens. A physician begins by making an incision in the eye to facilitate the insertion of surgical instruments. The physician uses surgical instruments such as choppers to break a cataract into smaller fragments so that a vacuum can aspirate the fragments to remove them from the eye via the incision. Once the fragments are removed, the physician inserts the artificial lens through the incision. Phacoemulsification is a type of cataract surgical procedure that uses ultrasound to emulsify the cataract. In particular, a physician inserts a phacoemulsification tip to the location of the cataract, and the phacoemulsification tip vibrates at an ultrasonic frequency to break down the cataract. The phacoemulsification tip includes a lumen (a hollow cavity) such that cataract fragments can be vacuumed out of the eye through the phacoemulsification tip. Phacoemulsification can also be completed without ultrasound using a phacoemulsification tip by mechanically breaking up the cataract and aspirating through the tip.

Existing phacoemulsification and other types of aspiration tips often become clogged with fragments of cataracts or other anatomical tissues that are too large to pass through the lumen of the tip, or become stuck to the tip. Thus, the physician must dislodge the blockages using irrigation, probing, or ultrasound power, which delays the surgical procedure. In some cases, fragments that are close in size to the diameter of the lumen travel slowly out of the tip. Thus, these phacoemulsification tips are inefficient at removing fragments from the eye and may require more ultrasound energy and power for a vacuum to aspirate the fragments. The application of ultrasound may cause damage to the eye by killing fragile non-reproducing endothelial cells of the cornea. Thus, it is desirable to shorten the duration of a phacoemulsification procedure by using phacoemulsification tips that can quickly remove the fragments from the eye and can do this without having blockages.

SUMMARY

A phacoemulsification or aspiration tip is designed for use in cataract surgeries such as phacoemulsification. The phacoemulsification tip (also referred to as a phaco tip) can reduce the duration of cataract surgeries because the phaco tip is designed to reduce the likelihood that cataract fragments from an eye of a patient will become clogged inside the phaco tip. Thus, the phaco tip can quickly remove fragments from the patient's eye. For example, the phaco tip has a lumen with variable sized diameters, which helps filter out larger cataract fragments that are more likely to clog the phaco tip. Further, the phaco tip can have a larger diameter at a bend to prevent blockages. The opening of the phaco tip can have a sharp edge to shear cataract fragments into smaller pieces that are less likely to clog the phaco tip. By preventing blockages using the phaco tip and reducing the duration of cataract surgeries, patients may recover faster from the cataract surgeries.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Particular embodiments as described herein relate to phacoemulsification tips, which may also be referred to as phaco tips, phacoemulsification probes, phaco probes, phacoemulsification needles, phaco needles, vacuum tips, or aspiration tips. The phaco tips described herein may be used in surgical procedures with or without ultrasound. For example, in a phacoemulsification surgical procedure, the phaco tip is used with ultrasound to emulsify a cataract into smaller fragments. The cataract can also be mechanically broken into smaller fragments without using ultrasound and aspirated with an aspiration tip. On the other hand, in a laser cataract surgical procedure, the phaco tip is used without ultrasound. Instead, a laser is used to break down cataracts and the phaco tip helps remove the resulting cataract fragments via vacuum suction. The fragments of cataracts or fragments of other anatomical tissues (e.g., corneal tissue) that are produced during a surgical procedure are referred to as fragments herein. In some procedures, no energy is applied to the eye with the tip, and in this case the vacuum or aspiration tip only aspirates the fragments of the cataract without also performing an emulsification.

The figures are not necessarily drawn to scale. In particular, certain features of phaco tips have been enlarged for purposes of illustration and clarity. In practice, the diameter of the phaco tips described herein have a diameter of approximately 0.4 to 1.9 millimeters in the narrowest ranges and 0.5 to 2 millimeters in the widest ranges. For instance, the diameter of a phaco tip is, e.g., 0.7 millimeters, within the narrowest range toward the opening of the phaco tip and, e.g., 0.9 millimeters, within the widest range toward a proximal end, i.e., further away from the opening, of the phaco tip. The diameter of the opening of the phaco tip is approximately 0.4 to 1.9 millimeters or approximately 0.6 to 1 millimeters. The thickness of the wall of the phaco tips is approximately 0.1 to 0.5 millimeters. The lumens of the phaco tips are typically in between 0.5 and 1.1 millimeters in diameter.

I. Prior Art Phaco Tips

Figure 1A:
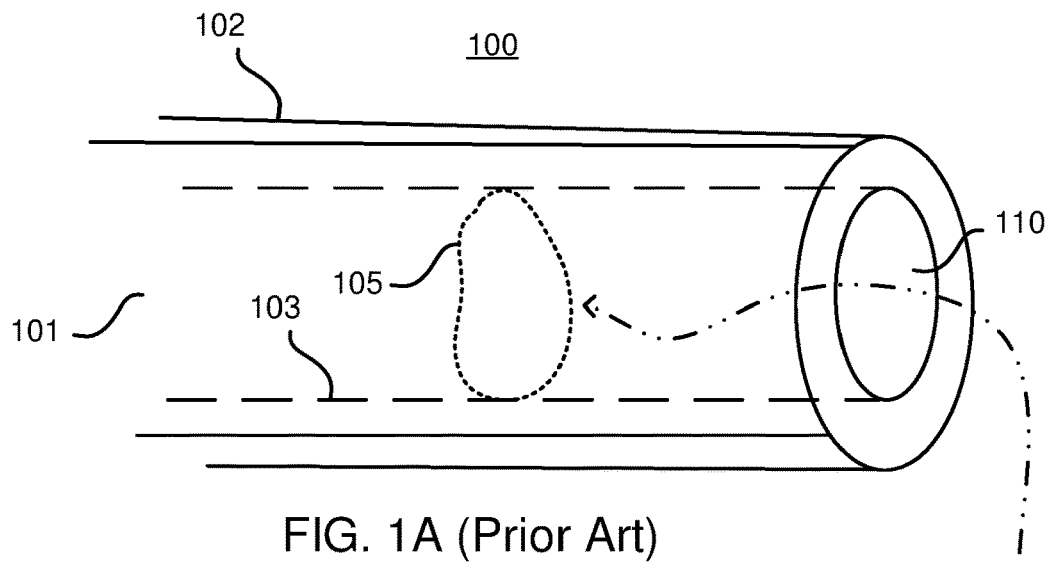
FIG. 1A shows a prior art phaco tip with a constant diameter according to one embodiment.

FIG. 1A shows a prior art phaco tip 100 with a constant diameter according to one embodiment. The phaco tip 100 includes an exterior wall 102 and an interior or inner wall 103, which form a lumen 101 of the phaco tip 100. The lumen 101 also has a constant diameter. The opening 110 of the tip allows fragments 105 to enter the phaco tip 100, e.g., via vacuum force. Further, the plane of the opening 110 is perpendicular to the body of the phaco tip 100. Fragments 105 that are similar to the size of the lumen 101 or larger in size than the lumen 101 may form a blockage in the lumen 101.

Figure 1B:
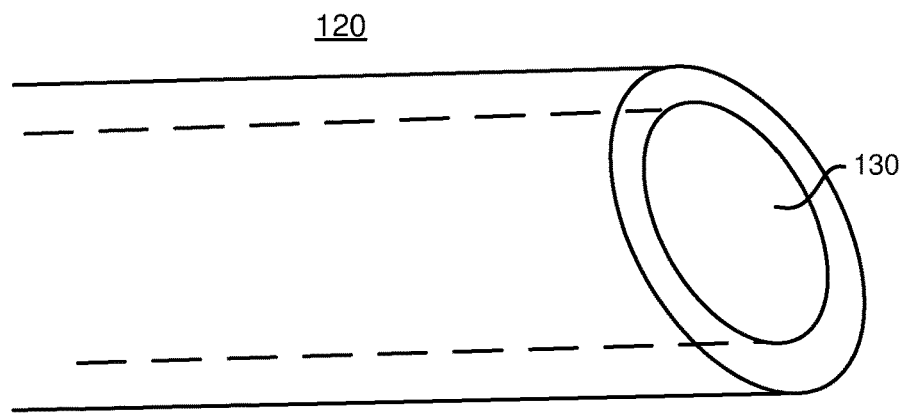
FIG. 1B shows a prior art phaco tip with a constant diameter and an oblique opening according to one embodiment.

FIG. 1B shows a prior art phaco tip 120 with a constant diameter and an oblique opening 130 according to one embodiment. The phaco tip 120 is similar to the phaco tip 100 shown in FIG. 1A. However, the phaco tip 120 has an opening 130 that is not perpendicular, i.e., oblique, to the body of the phaco tip 120.

Figure 1C:
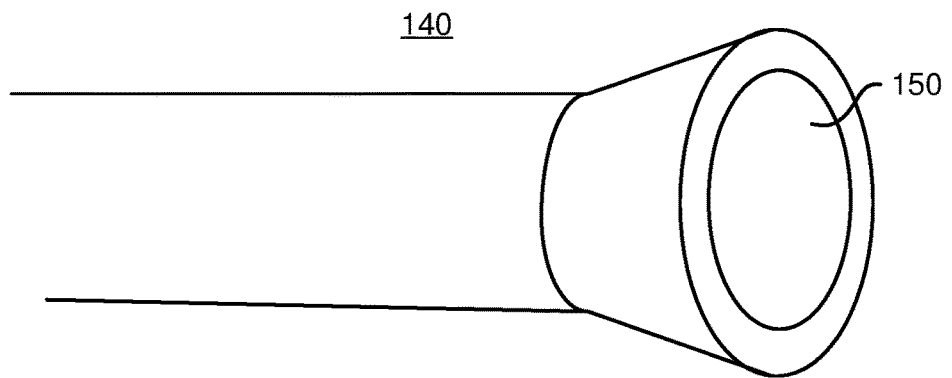
FIG. 1C shows a prior art phaco tip with a flared opening according to one embodiment.

FIG. 1C shows a prior art phaco tip 140 with a flared opening 150 according to one embodiment. In particular, the diameter of the phaco tip 140 and the lumen of the phaco tip 140 gradually increase toward the flared opening 150. Compared to the opening 110 of the phaco tip 100 shown in FIG. 1A, the flared opening 150 has a larger surface area. Thus, the phaco tip 140 can vacuum larger sized fragments, relative to the phaco tip 100, but the larger fragments tend to get stuck in the lumen of phaco tip 140 because the lumen has a smaller diameter than the opening 150.

II. Narrowing Diameter at Tip Opening

Figure 2A:
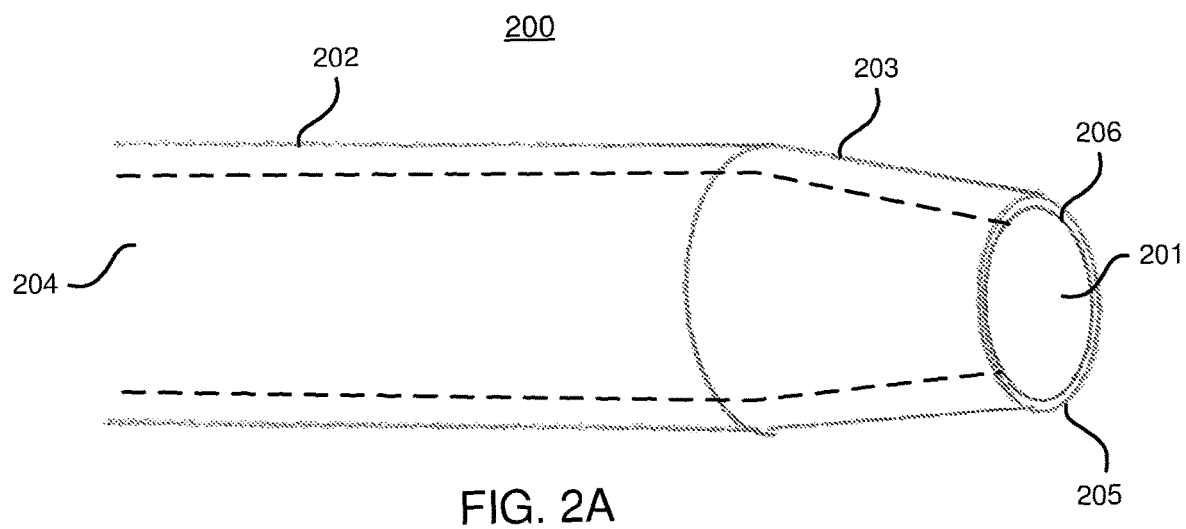
FIG. 2A shows a phaco tip with a tapered diameter at the opening according to one embodiment.

FIG. 2A shows a phaco tip 200 with a tapered diameter at the opening 201 according to one embodiment. In particular, the phaco tip 200 and the lumen 204 of the phaco tip 200 include a straight section 202 and a tapered section 203. In the straight section 202, the phaco tip 200 and the lumen 204 have a constant diameter. In the tapered section 203, the diameter of the phaco tip 200 and the lumen 204 gradually decreases toward the opening 201. The thickness of the wall of the phaco tip 200 may either be constant or differ between the straight section 202 and the tapered section 203.

The opening 201 includes an outer edge 205 and an inner edge 206. The outer edge 205 and/or inner edge 206 may be sharp. Thus, the outer edge 205 and/or inner edge 206 can shear fragments during a surgical procedure, including fragments that become stuck to the phaco tip 200 near the opening 201. As a result, there is a reduced likelihood that fragments will clog the phaco tip 200 (due to prevention of fragments staying stuck near the opening 201 and/or shearing fragments into smaller pieces), which helps reduce the time required to complete the surgical procedure. In some embodiments, the outer edge 205 and/or the inner edge 206 are dull instead of sharp. Though the opening 201 shown in FIG. 2A is circular shaped, it should be noted that phaco tips may have openings of different shapes, e.g., elliptical, square, any other type of polygon, an arbitrary shape, etc.

The tapered section 203 may be advantageous, e.g., because the tapered section 203 reduces friction and resistance experienced by the phaco tip 200 during a surgical procedure. In particular, since the opening 201 at the end of the tapered section 203 has a smaller diameter than the straight section 202, the tapered section 203 is less likely to contact or move against surfaces inside an eye during the surgical procedure, compared to a phaco tip with a constant diameter. Further, a physician can more easily manipulate the phaco tip 200 around more confined areas inside the eye. The tapered section 203 also provides the physician more visibility inside the eye when performing the surgical procedure because the smaller diameter of the tapered section 203 obscures less of the physician's line of sight relative to the straight section 202. Another advantage of the tapered section 203 is that it is less likely that fragments will be clogged inside the lumen 204 because fragments that enter the lumen 204 through the opening 201 are smaller in diameter (at least in one dimension) than the diameter of the lumen 204 in the straight section 202.

Figure 2B:
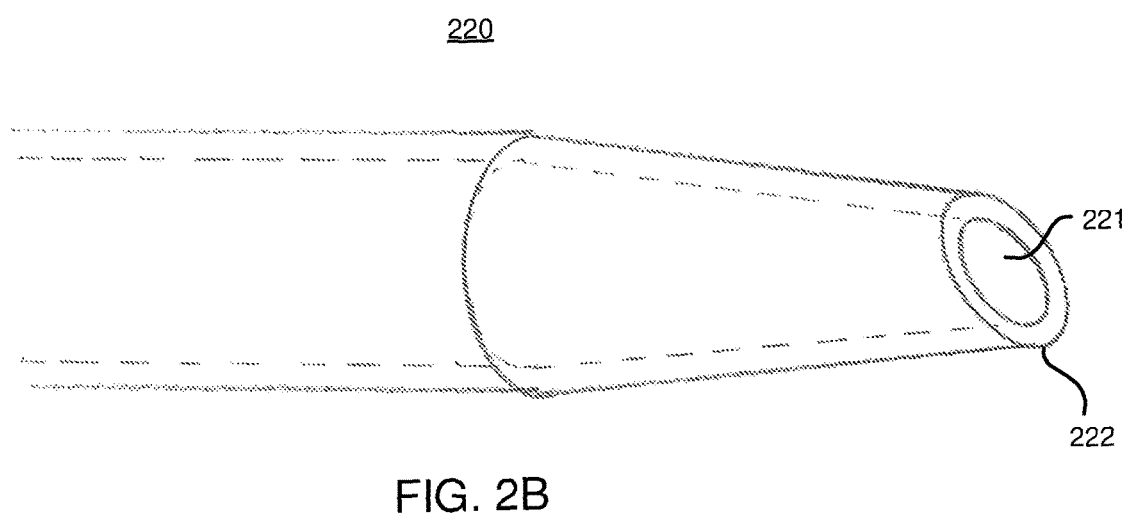
FIG. 2B shows another phaco tip with a tapered diameter at the opening according to one embodiment.

FIG. 2B shows another phaco tip 220 with a tapered diameter at the opening 221 according to one embodiment. The phaco tip 220 is substantially the same as the phaco tip 200 shown in FIG. 2B, except that the phaco tip 220 has an oblique opening 221 while the phaco tip 200 has an opening 201 perpendicular to the body of the phaco tip 200. Compared to the opening 201 of the phaco tip 200, the oblique opening 221 has a larger surface area. Thus, the phaco tip 220 can vacuum larger sized fragments, relative to the phaco tip 200. In some embodiments, the angle of the oblique opening 221 is less than 60 degrees (relative to a plane perpendicular to the body of the phaco tip 220) such that the oblique opening 221 does not obscure the line of sight of a physician using the phaco tip 220 while performing a surgical procedure. Further, the oblique opening 221 provides a sharp end 222 of the phaco tip 220, which helps a physician break down or manipulate (e.g., by impaling) fragments.

III. Narrowing Lumen Diameter at Tip Opening

Figure 3A:
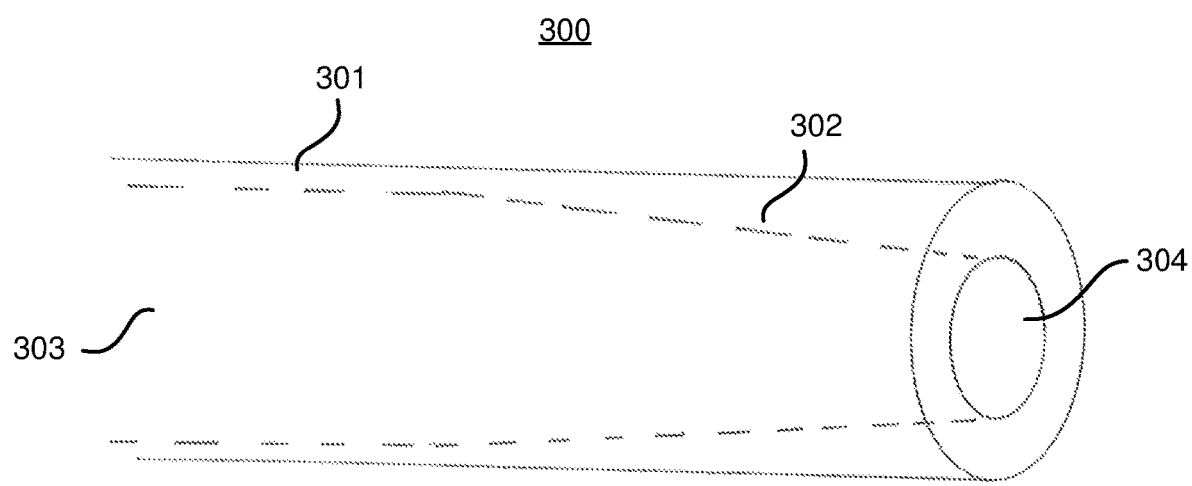
FIG. 3A shows a phaco tip with a constant outer diameter and a lumen with a tapered diameter at the opening according to one embodiment.

FIG. 3A shows a phaco tip 300 with a constant outer diameter and a lumen 303 with a tapered diameter at the opening 304 according to one embodiment. Similar to the phaco tip 200 shown in FIG. 2A, the lumen 303 includes a straight section 301 and a tapered section 302. The diameter of the lumen 303 gradually decreases toward the opening 304. Unlike the phaco tip 200, the outer diameter of the phaco tip 300 remains constant. Thus, the thickness of the wall of the phaco tip 300 gradually increases toward the opening 304.

Figure 3B:
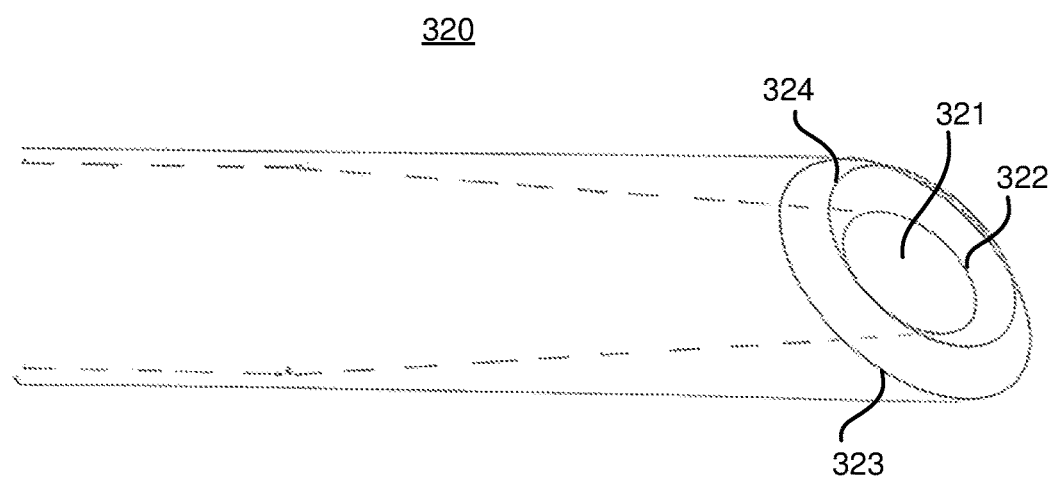
FIG. 3B shows another phaco tip with a constant outer diameter and a lumen with a tapered diameter at the opening according to one embodiment.

FIG. 3B shows another phaco tip 320 with a constant outer diameter and a lumen 303 with a tapered diameter at the opening 304 according to one embodiment. The phaco tip 320 is similar to the phaco tip 300 shown in FIG. 3B, though the phaco tip 320 has an oblique opening 321, while the phaco tip 300 has an opening 304 perpendicular to the body of the phaco tip 300. In addition, the oblique opening 321 has an inner edge 322 and an outer edge 323, which may be sharp. The oblique opening 321 also has a raised edge 324 between the inner edge 322 and the outer edge 323. The raised edge 324 can be a sharp blade that helps break down fragments.

Figure 4A:
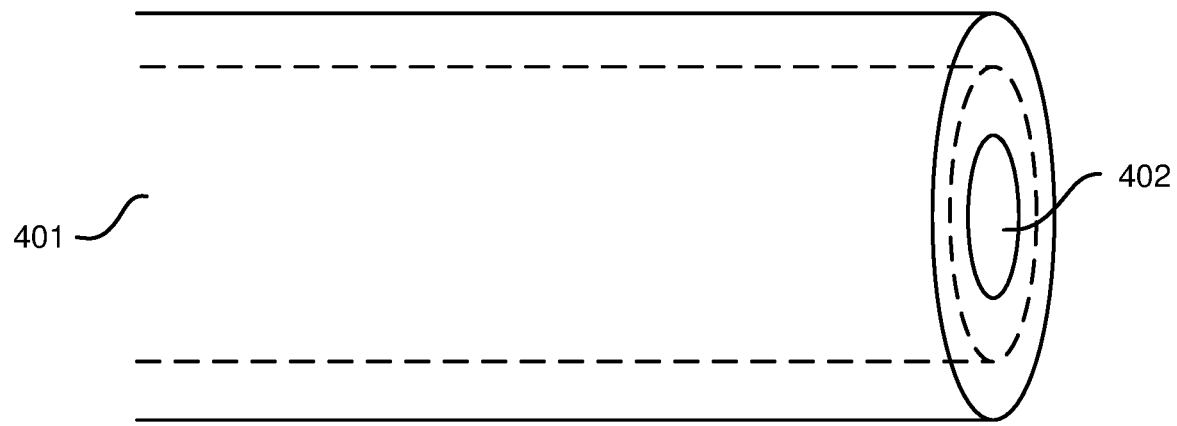
FIG. 4A shows a phaco tip with a smaller diameter opening according to one embodiment.

FIG. 4A shows a phaco tip 400 with a smaller diameter opening 402 according to one embodiment. In particular, the diameter of the opening 402 is smaller than the diameter of the lumen 401 of the phaco tip 400. An advantage of the smaller diameter opening 402 is that, similar to the phaco tip 200 shown in FIG. 2A, it is less likely for fragments to become clogged inside the phaco tip 400 because fragments that enter the lumen 401 through the opening 402 are smaller in diameter (at least in one dimension) than the diameter of the lumen 401.

Figure 4B:
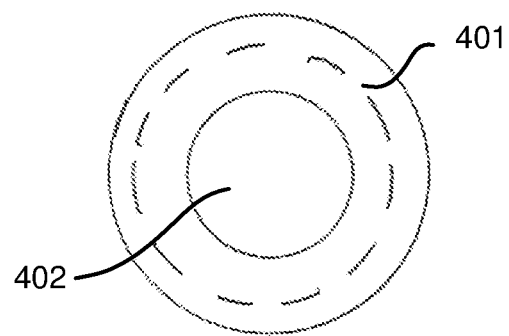
FIG. 4B shows a front view of the phaco tip shown in FIG. 4A according to one embodiment.

FIG. 4B shows a front view of the phaco tip 400 shown in FIG. 4A according to one embodiment. FIG. 4B further illustrates that the diameter of the opening 402 is smaller than the diameter of the lumen 401.

IV. Variable Lumen Diameter

Figure 5A:
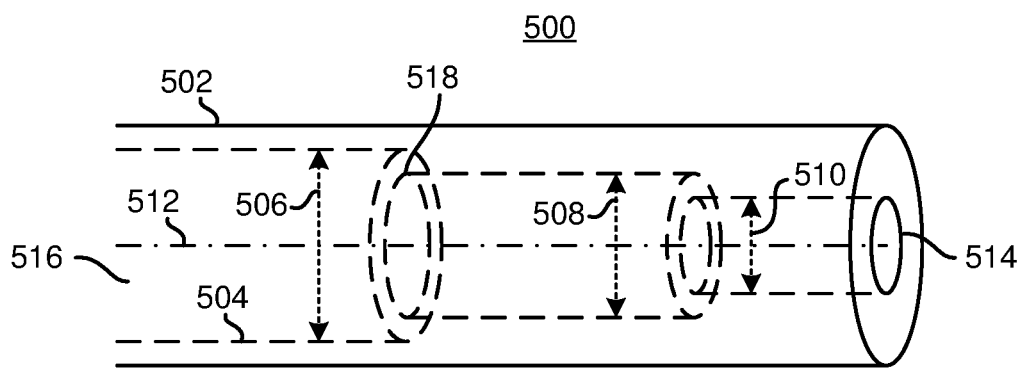
FIG. 5A shows a phaco tip with variable lumen diameters according to one embodiment.

FIG. 5A shows a phaco tip 500 with variable lumen diameters according to one embodiment. The phaco tip 500 includes an outer wall 502 with a constant diameter and an inner wall 504 that defines a lumen 516 of the phaco tip 500. The lumen 516 has a first diameter 506, second diameter 508, and third diameter 510 along the length of the phaco tip 500. In the example shown in FIG. 5A, the first diameter 506 is larger than the second diameter 508, which is larger than the third diameter 510. In other embodiments, the lumen 516 may include additional, fewer, or different sized variable diameters, e.g., four different diameters where the first and third diameters are equal to each other, and where the second and fourth diameters are equal to each other. Each section of the lumen 516 corresponding to the diameters 506, 508, and 510 are concentric to the phaco tip 500, e.g., the cylinder defined by the outer wall 502 with centerline 512 (e.g., a longitudinal axis). In other embodiments, one or more sections (with different diameters) of the lumen 516 may not necessarily be concentric to the phaco tip 500.

Typically, the diameter of the lumen 516 is smaller toward the opening 514 of the phaco tip 500. Thus, it is less likely for fragments to become clogged inside the phaco tip 500 because fragments that enter the lumen 500 through the opening 514 are smaller in diameter (at least in one dimension) than one or more of the sections of the lumen 516 with variable diameters. In some embodiments, another advantage of the variable diameter lumen 516 is that the edge between two sections of the lumen 516 with different diameters, e.g., edge 518, is sharp. Thus, the sharp edge 518 can shear and chop fragments into smaller pieces as the fragments are vacuumed through the lumen 516 and/or prevent fragments from becoming stuck along the inner wall 504.

Figure 5B:
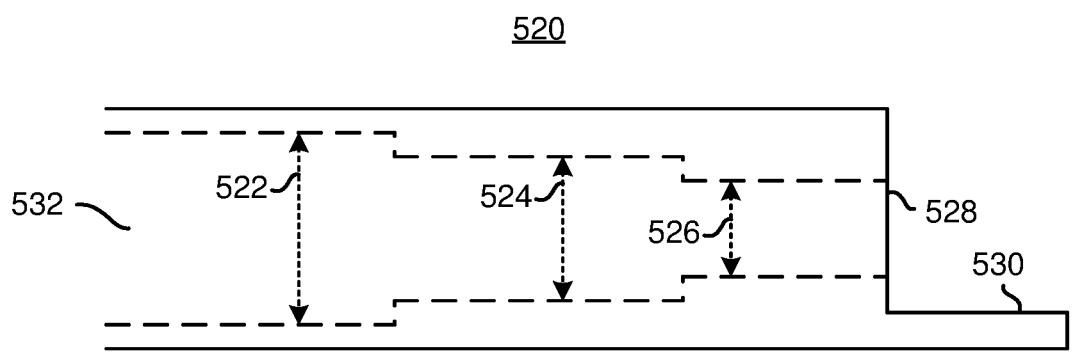
FIG. 5B shows a side view of another phaco tip with variable lumen diameters according to one embodiment.

FIG. 5B shows a side view of another phaco tip 520 with variable lumen diameters according to one embodiment. Similar to the phaco tip 500 shown in FIG. 5A, the phaco tip 520 includes a lumen 532 with a first diameter 522, a second diameter 524, and a third diameter 526. The phaco tip 520 also includes a protrusion 530 at the opening 528 of the phaco tip 520. The protrusion 530 may have one or more sharp edges, e.g., to help break fragments into smaller pieces or impale fragments.

Figure 5C:
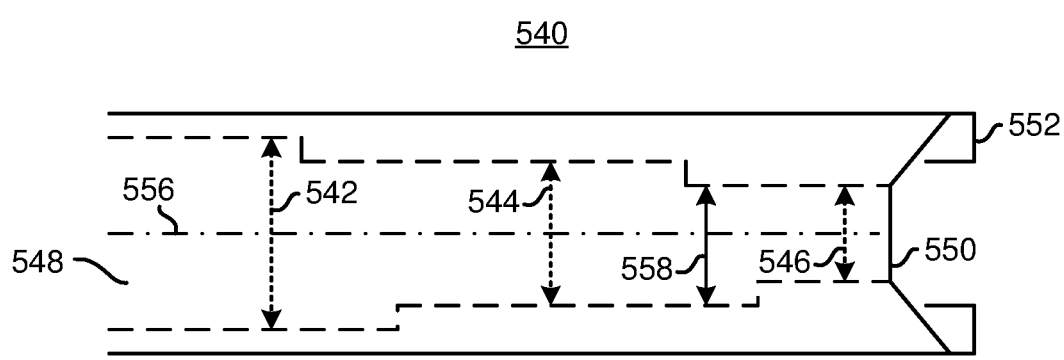
FIG. 5C shows a side view of yet another phaco tip with variable lumen diameters according to one embodiment.

FIG. 5C shows a side view of yet another phaco tip 540 with variable lumen diameters according to one embodiment. Similar to the phaco tip 500 shown in FIG. 5A, the phaco tip 540 includes a lumen 548 with a first diameter 542, a second diameter 544, and a third diameter 546. However, unlike the phaco tip 500, not all sections of the lumen 548 are concentric to the phaco tip 540. For example, section 558 of the lumen 548 is not concentric to the phaco tip 540, i.e., the center of the circle defined by the lumen 548 at section 558 does not intersect the centerline 556 of the phaco tip 540 (e.g., a longitudinal axis). The phaco tip 540 includes sharp edges 552 near the opening 550 of the phaco tip 540, e.g., to help break fragments into smaller pieces as the fragments are vacuumed into the phaco tip 540. The opening 550 also has a funnel shape that leads to the section of the lumen 548 that has the third diameter 546.

V. Phaco Tips With a Bend

Figure 6A:
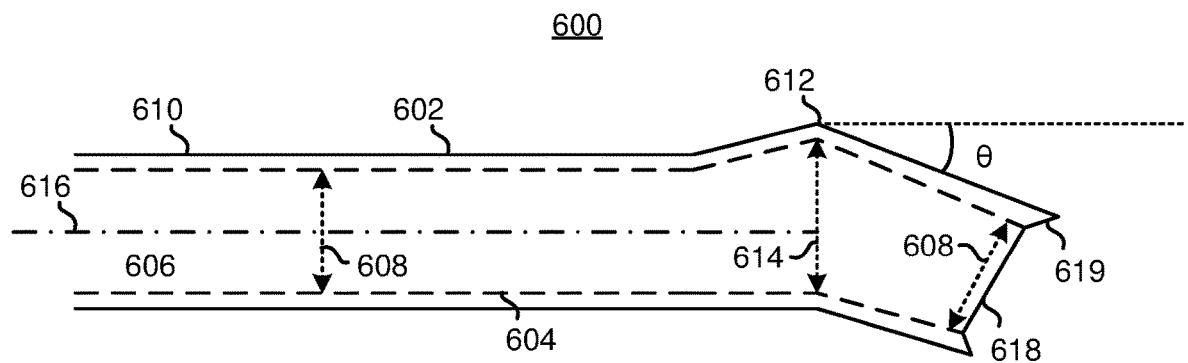
FIG. 6A shows a side view of a phaco tip with a bend according to one embodiment.

FIG. 6A shows a side view of a phaco tip 600 with a bend according to one embodiment. The phaco tip 600 includes an exterior wall 602 and an inner wall 604, which form the lumen 606 of the phaco tip 600. The lumen 606 has a constant diameter 608 in the straight section 610 of the phaco tip 600. The diameter of the lumen 606 gradually increases toward the opening 618 of the lumen 606. In particular, the diameter 614 of the lumen 606 is larger than the constant diameter 608. The diameter 614 occurs at the bend 612 of the lumen 606. Note that the center of the circular cross section of the lumen 606 at the bend 612 does not necessarily intersect with the centerline 616 of the straight section 610, i.e., the diameter of the lumen 606 does not need to remain symmetric about the centerline 616. The increased diameter 614 at the bend 612 reduces the likelihood that fragments will become clogged in the lumen 640. The diameter of the lumen 606 gradually decreases from the bend 612 to the opening 618 to prevent larger fragments from entering the lumen 606 and forming potential blockages. In FIG. 6A, the diameter 608 of the lumen 606 at the opening 618 is the same as the diameter 608 in the straight section 610. In other embodiments, the diameter at the opening 618 may be smaller than the diameter 608.

The lumen 606 bends at an angle θ relative to a line parallel to the centerline 616 (e.g., a longitudinal axis). Typically, θ is in between 0 and 30 degrees, e.g., 12 degrees or 22 degrees. The lumen 606 includes a bevel 619 around the opening 618, e.g., an oblique opening. The angle of the bevel 619 may vary, e.g., 30 degrees of 45 degrees relative to a plane perpendicular to the opening 618. The bevel 619 may be advantageous, e.g., because the bevel 619 provides an angular opening 618 that allows fragments to more easily enter the lumen 606. In some embodiments, the bend 612 provides a larger field of view of a patient's eye for the physician using the phaco tip 600 while performing a surgical procedure, e.g., because the physician can orient the phaco tip 600 to avoid obscuring certain portions of the eye. In some embodiments, the bevel 619 is rounded or smooth such that the phaco tip 600 is less likely to damage tissue of a patient's eye.

Figure 6B:
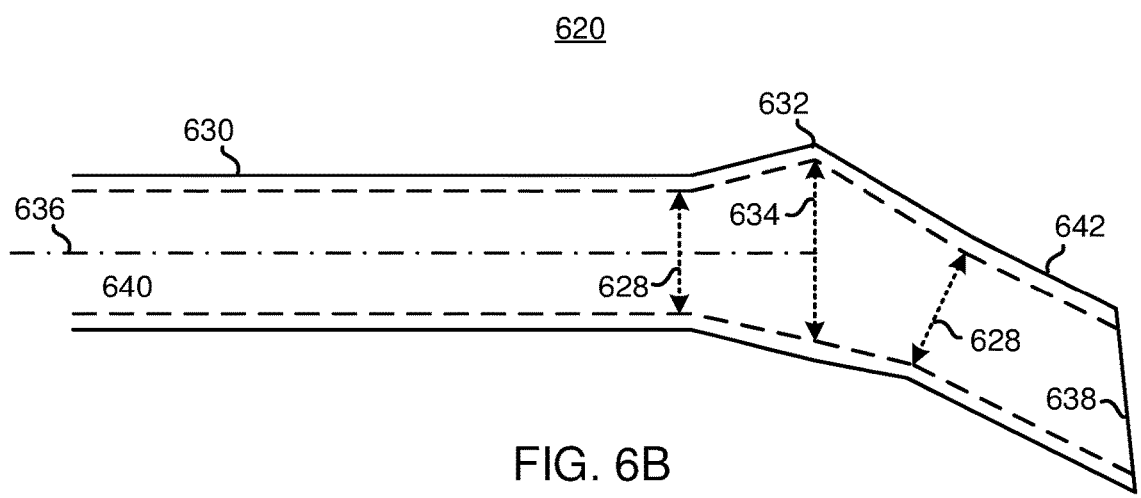
FIG. 6B shows a side view of another phaco tip with a bend according to one embodiment.

FIG. 6B shows a side view of another phaco tip 620 with a bend according to one embodiment. Similar to the phaco tip 600 shown in FIG. 6A, the phaco tip 620 includes a lumen 640 that has a constant diameter 628 in the straight section 630 of the phaco tip 620. The lumen 640 also bends at an angle relative to the straight section 630. Further, the diameter of the lumen 640 gradually increases toward the bend 632 of the lumen 640. In particular, the diameter 634 of the lumen 640 at the bend 632 is larger than the constant diameter 628. Unlike the lumen 606 shown in FIG. 6A, the diameter of the lumen 640, from the straight section 630 to the bend 632, remains symmetric about the centerline 636 of the straight section 630. In addition, the distal section 642 of the lumen 640 between the bend 632 and the opening 638 also has a constant diameter 628. In some embodiments, the diameter of the distal section 642 is not necessarily equal to the constant diameter 628 of the straight section 630.

VI. Phaco Tip With a Funnel Opening

Figure 7:
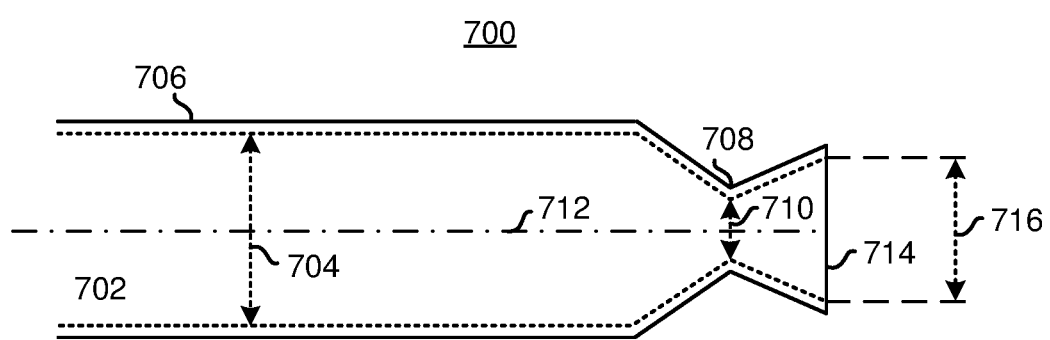
FIG. 7 shows a phaco tip with a funnel opening according to one embodiment.

FIG. 7 shows a phaco tip 700 with a funnel opening 714 according to one embodiment. The phaco tip 700 includes a lumen 702 with a constant diameter 704 along a straight section 706 of the phaco tip 700. The diameter of the lumen 702 gradually decreases until the section 708 of the phaco tip 700. The diameter 710 of the lumen 702 is smaller than the constant diameter 704. From the section 708, the diameter of the lumen 702 gradually increases, which forms the funnel opening 714. The diameter 716 of the funnel opening 714 is larger than the diameter 710 and smaller than the constant diameter 704. In other embodiments, the diameter 716 is equal to the constant diameter 704. The funnel opening 714 reduces the likelihood that fragments will become clogged inside the lumen 702 because fragments that pass through the diameter 710 are smaller (at least in one dimension) than the constant diameter 704. In other words, the funnel opening 714 acts as a filter to prevent fragments that are too large from entering the straight section 706 of the phaco tip 700. In addition, a physician may be able to more easily aim or position the phaco tip 700 to aspirate fragments inside a patient's eye because the funnel opening 714 has a larger outer diameter 716.

This presented invention can be used with or without an ultrasound system. Typically, a phaco tip includes a sleeve that surrounds the phaco tip and provides an irrigation solution, e.g., a balanced Salt Solution (BSS). The irrigation solution enters the eye through the sleeve to maintain intraocular pressure (e.g., to maintain the anterior chamber shape of the eye) and cool the phaco tip. The heat generated by ultrasound during phacoemulsification can burn the surrounding tissue if the phaco tip is not cooled with the irrigation solution. The phaco tips described herein reduce the likelihood that fragments will form blockages in the phaco tips, which allows irrigation solution to flow through the phaco tips to an operative site of a surgical procedure. In some embodiments, a different source of irrigation solution can be used, which may improve the fluid-dynamics of cataract surgery. Though not shown in the figures, the phaco tips described herein can be connected to a pump or other systems used to create vacuum or suction in the phaco tips to aspirate fragments from a patient's eye.

Various different types of choppers can be used with any of the phaco tip embodiments of the invention described herein. In one embodiment, the chopper is designed to be used without application of ultrasound or laser energy to the eye, such as the chopper described in U.S. Provisional Application No. 62/190,190, filed on Jul. 8, 2015, which is hereby incorporated by reference herein in its entirety. The chopper has an angle at a bend of less than 90 degrees that allows for posterior approach to a cataract inside an eye and more efficient breakage such that energy is not required in the eye for further fragmentation or emulsification of the cataract.

VII. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the apparatus disclosed herein without departing from the spirit and scope defined in the appended claims. In particular, features such as oblique openings (e.g., shown in FIG. 1B), tapered openings (e.g., shown in FIG. 2A), tapered lumens (e.g., shown in FIG. 3A), narrower openings (e.g., shown in FIG. 4A), lumens with variable diameters (e.g., shown in FIGS. 5A-C), lumens with wider openings at bends (e.g., shown in FIGS. 6A-B), or funnel openings (e.g., shown in FIG. 7), may be used in any of the phaco tip embodiments or designs described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A phacoemulsification tip for cataract surgery comprising:
    an exterior wall and an interior wall forming a tubular structure having a length, the length including a first sub-length, a second sub-length, and a third sub-length;
    a lumen formed by the interior wall, comprising:
        a first section having a first constant diameter along the first sub-length;
        a second section adjacent to the first section, the second section having a second constant diameter along the second sub-length, the second constant diameter smaller than the first constant diameter; and a third section adjacent to the second section, the third section having a third constant diameter along the third sub-length, the third constant diameter smaller than the second constant diameter; and an opening into the lumen, wherein the opening is adjacent to the third section, wherein the exterior wall has a fourth constant diameter along the first sub-length, the second sub-length, and the third sub-length, and wherein the fourth constant diameter is greater than the first constant diameter.

2. The phacoemulsification tip of claim 1, wherein the first section, the second section, and the third section are concentric.

3. The phacoemulsification tip of claim 1, wherein the first section and the second section are not concentric.

4. The phacoemulsification tip of claim 1, further comprising a protrusion at the opening.

5. The phacoemulsification tip of claim 4, wherein the protrusion includes one or more sharp edges.

6. The phacoemulsification tip of claim 4, wherein the protrusion is configured to emulsify a cataract using ultrasound.

7. The phacoemulsification tip of claim 1, wherein the opening includes a funnel.

8. The phacoemulsification tip of claim 1, wherein a plane of the opening is angled relative to a longitudinal axis of the lumen.

9. The phacoemulsification tip of claim 1, wherein the opening has a diameter between 0.4 and 1.9 millimeters.

10. The phacoemulsification tip of claim 1, wherein a thickness between the exterior wall and the interior wall varies from the first sub-length to the second sub-length, and varies from the second sub-length to the third sub-length.

11. The phacoemulsification tip of claim 10, wherein the thickness is between 0.1 and 0.5 millimeters.

\* \* \* \* \*